US00PP37809P2

(12) United States Plant Patent
Gee

(10) Patent No.: US PP37,809 P2
(45) Date of Patent: Oct. 20, 2026

(54) ***PRUNUS* PLANT NAMED 'GEE001'**

(50) Latin Name: ***Prunus* hybrid**
Varietal Denomination: GEE001

(71) Applicant: Kary Gee, Stockbridge, MI (US)

(72) Inventor: Kary Gee, Stockbridge, MI (US)

(73) Assignee: GEE FARMS NURSERY & GREENHOUSE LLC, Stockbridge, MI (US)

( * ) Notice: Subject to any disclaimer, the term of this patent is extended or adjusted under 35 U.S.C. 154(b) by 0 days.

(21) Appl. No.: 19/643,787

(22) Filed: Apr. 9, 2026

(51) Int. Cl.
*A01H 5/00* (2018.01)

(52) U.S. Cl.
USPC ..... Plt./182

(58) Field of Classification Search
USPC ..... Plt./156, 181, 182
See application file for complete search history.

(56) References Cited

U.S. PATENT DOCUMENTS

PP23,384 P2 * 2/2013 Dunn ..... A01H 6/7427
Plt./196

* cited by examiner

*Primary Examiner* — Karen M Redden
(74) *Attorney, Agent, or Firm* — Penny J. Aguirre

(57) ABSTRACT

A new cultivar of *Prunus* hybrid tree named 'GEE001' that is characterized by its flower buds that are pink in color and open to flowers that are white and blushed with pink in color and its foliage that emerges apricot in color, changing to variegation green, yellow, and white in color and maturing to variegation green and white in color.

4 Drawing Sheets

Botanical classification: *Prunus* hybrid.
Variety denomination: 'GEE001'.

BACKGROUND OF THE INVENTION

The present invention relates to a new and distinct cultivar of *Prunus* hybrid and will be referred to hereafter by its cultivar name, 'GEE001'. 'GEE001' is a new cultivar of sweet cherry tree grown an ornamental landscape.

The new cultivar was discovered by the Inventor in May of 2021 as a naturally occurring branch mutation of *Prunus* 'Snofozam' (not patented) in a trial garden in Jackson, Michigan.

Asexual propagation of the new cultivar was first accomplished by chip budding by the Inventor in Boring, Oregon in August of 2021. Asexual propagation by chip budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'GEE001' as a unique cultivar of cherry tree.

1. 'GEE001' exhibits flower buds that are pink in color and open to flowers that are white and blushed with pink in color.
2. 'GEE001' exhibits foliage that emerges apricot in color, changing to variegation green, yellow, and white in color and maturing to variegation green and white in color.

The mutation parent of 'GEE001' differs from 'GEE001' in having white flowers and non-variegated foliage.

'GEE001' can be most closely compared to the cultivars *Prunus subhirtella* 'Pendula' (not patented) and *Prunus* x *yedoensis* 'Shidare-Yoshino' (not patented). 'Pendula' is similar to 'GEE001' in having flowers that are pink in color and a weeping plant habit. 'Pendula' differs from 'GEE001' in having flowers with more petals that are deeper pink in color, green leaves that are not variegated, and a larger plant size. 'Shidare-Yoshino' is similar to 'GEE001' in having a weeping plant habit. 'Shidare-Yoshino' differs from 'GEE001' in having white flowers, a larger plant size, and green foliage that are not variegated.

BRIEF DESCRIPTION OF THE DRAWINGS

The accompanying color photographs illustrate the overall appearance and distinct characteristics of the new *Prunus*. The photographs were taken of 1-year-old plants (from a rooted graft) of the new cultivar as grown in a garden in Jackson, Michigan.

The photograph in FIG. 1 provides a side view of 'GEE001'.

Figure 1:
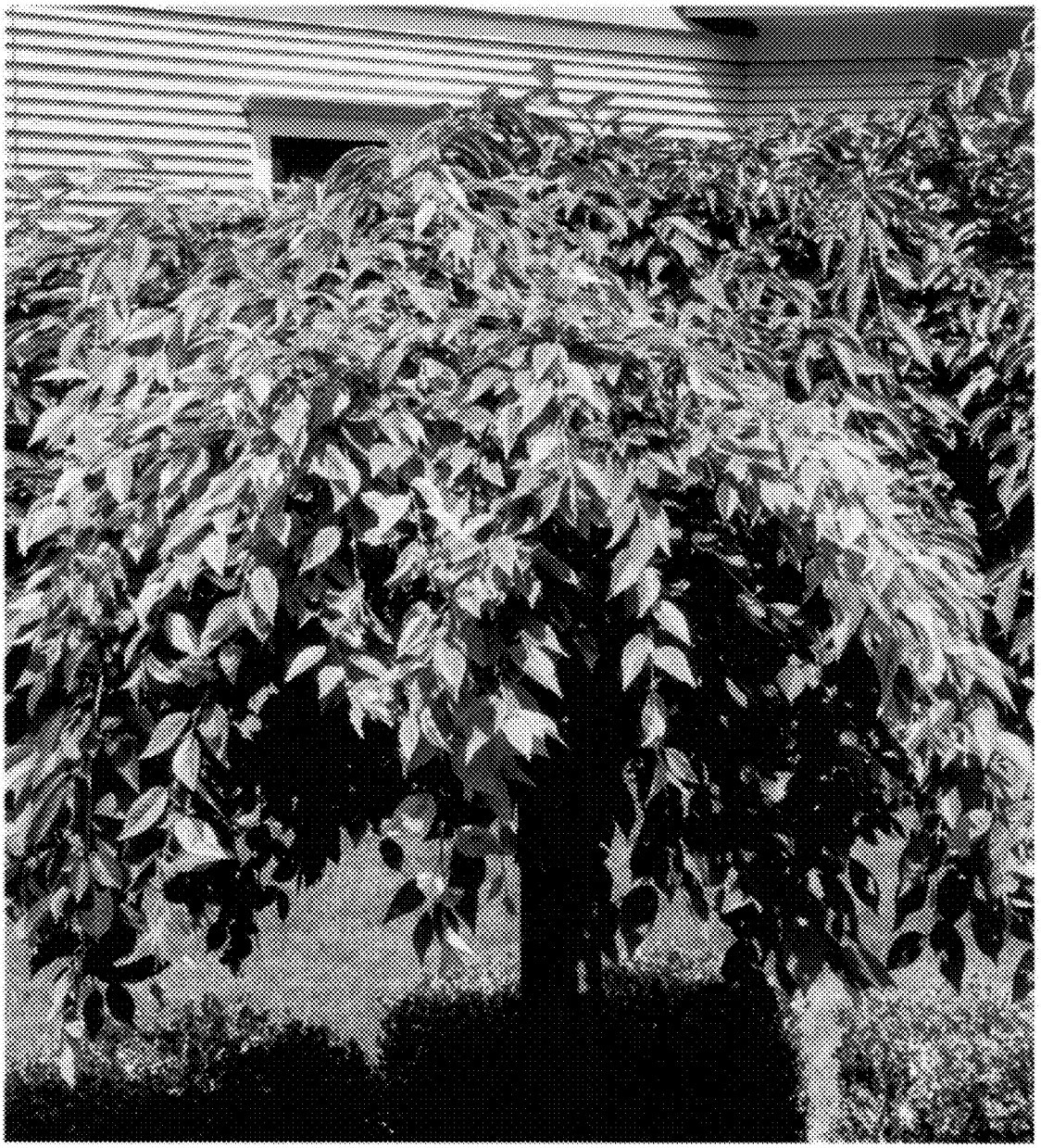
Figure 2:
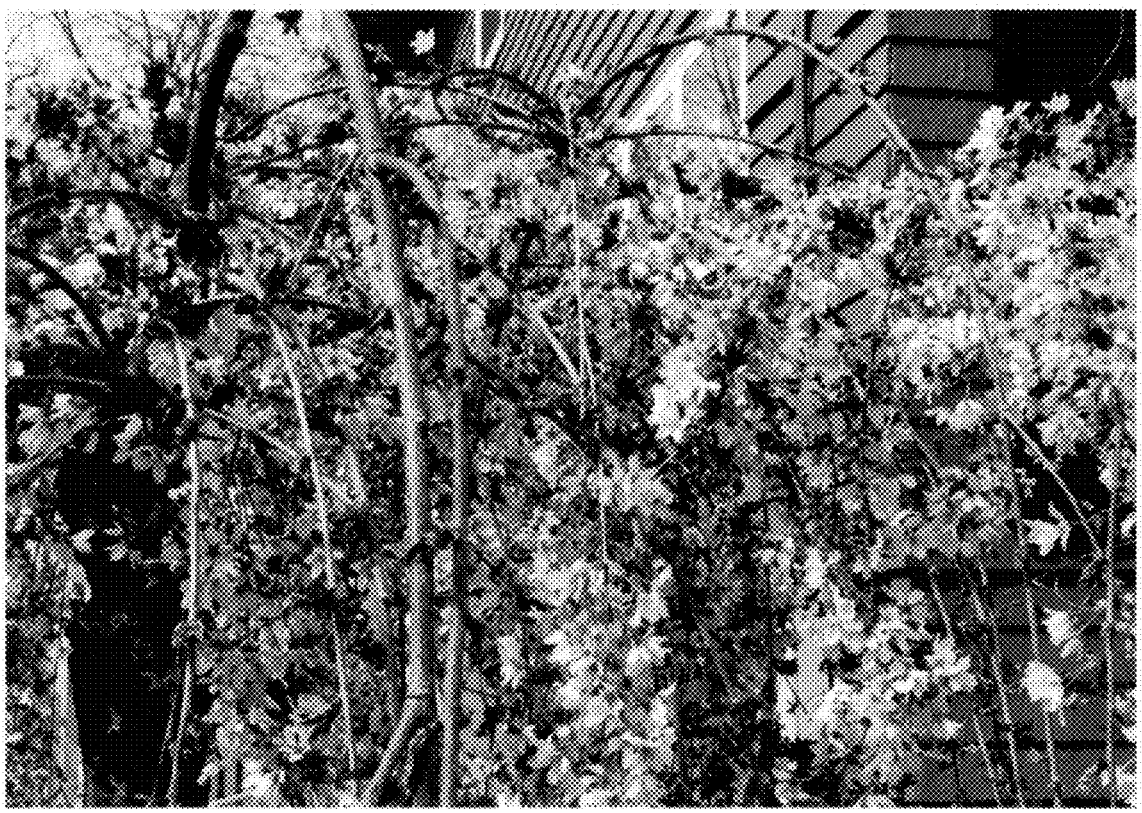

The photograph in FIG. 2 provides a close-up, side view of 'GEE001' in bloom.

Figure 3:
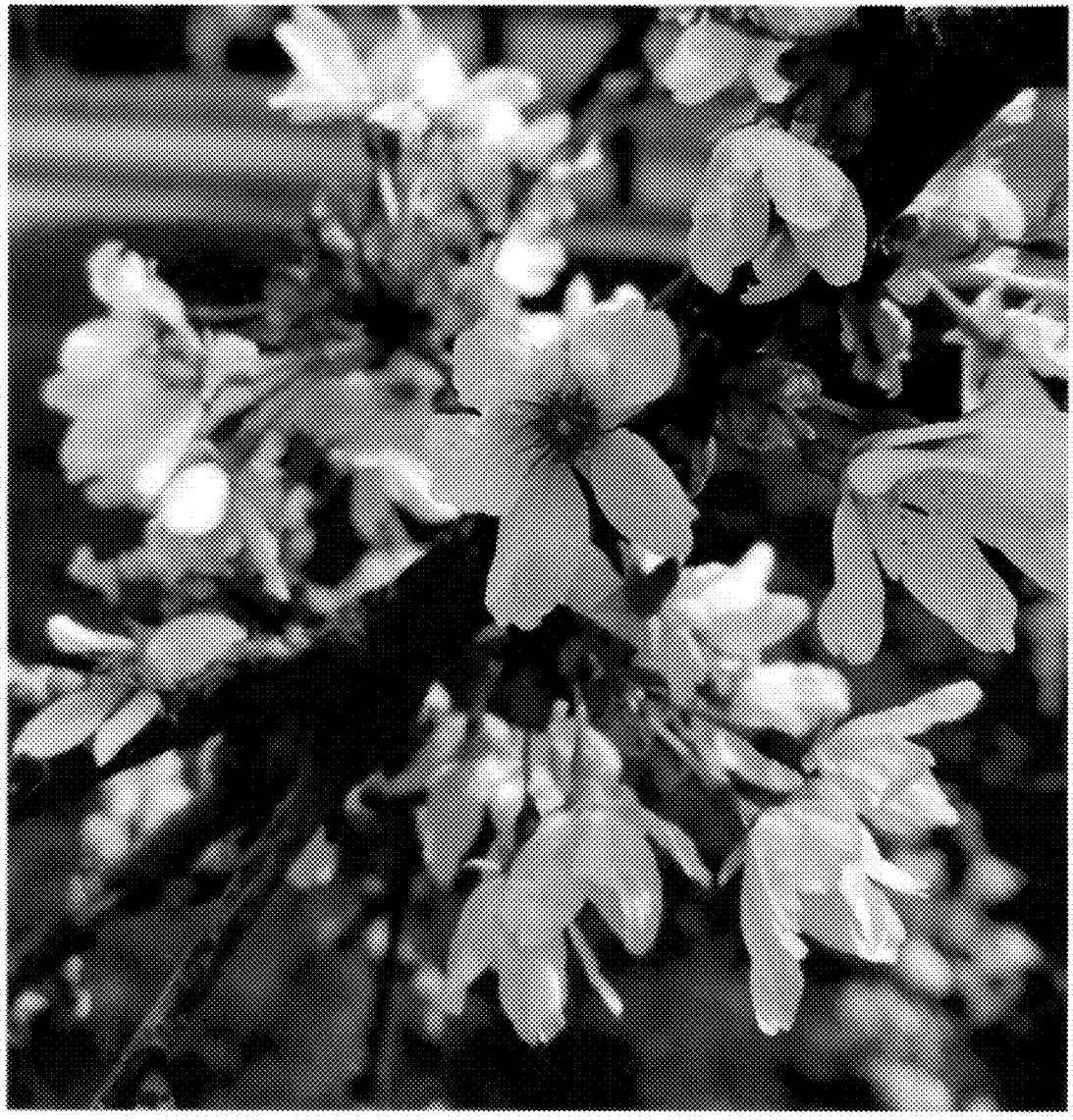

The photograph in FIG. 3 provides a close-up view of flowers of 'GEE001'.

Figure 4:
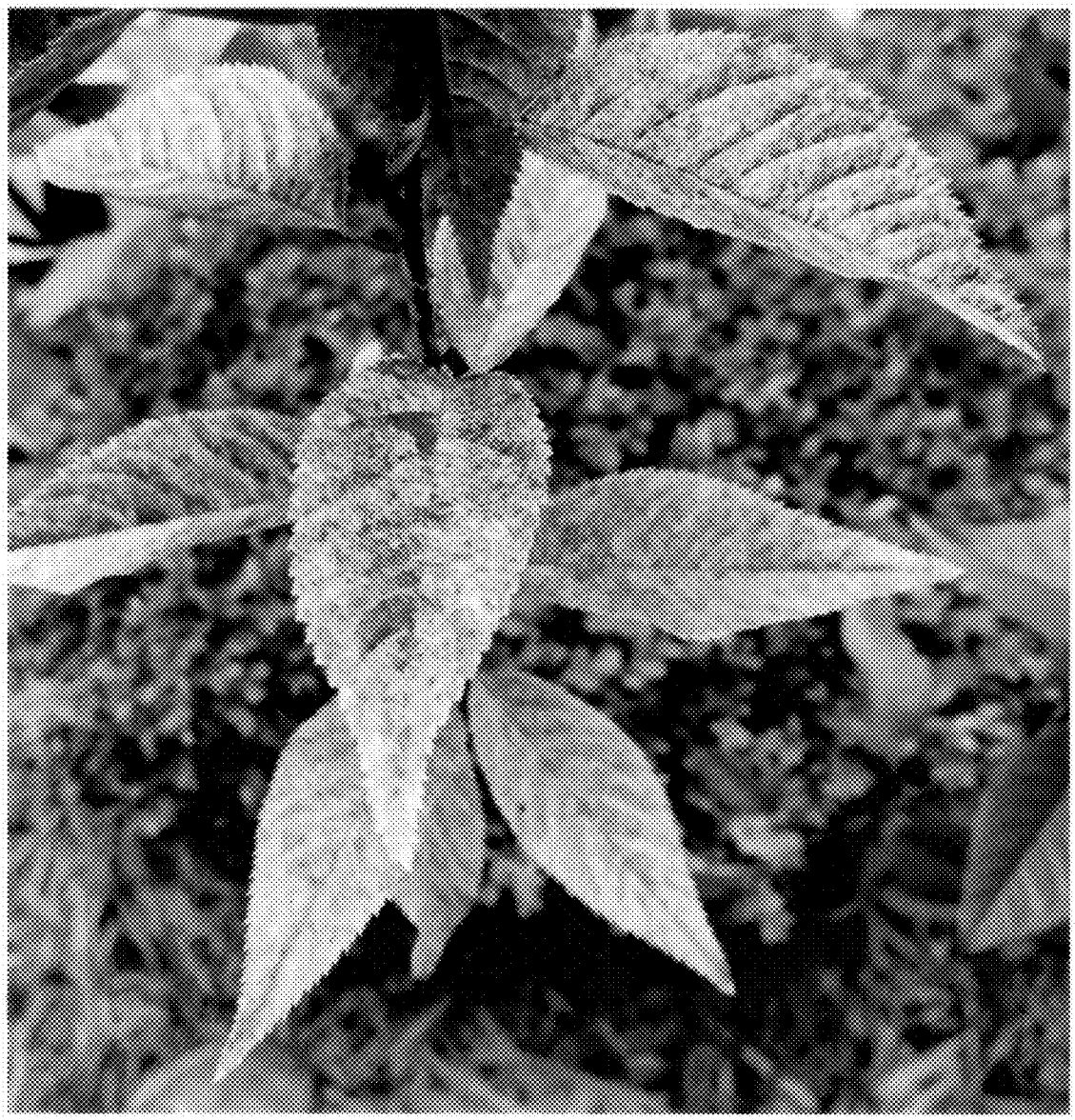

The photograph in FIG. 4 provides a close-up view of the foliage of 'GEE001'.

The colors in the photographs are as close as possible with the digital photography and printing techniques utilized and the color codes in the detailed botanical description accurately describe the new *Prunus*.

DETAILED BOTANICAL DESCRIPTION

The following is a detailed description of three-year-old plants the new *Prunus* as grown in 10-gallon containers in Jackson, Michigan. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—April in Oregon.

*Plant type*.—Deciduous tree.

*Plant habit*.—Weeping.

*Height and spread*.—Reaches about 3 m in height and about 2.4 m in spread.

*Hardiness*.—At least in U.S.D.A. Zones 5 to 8.

*Diseases and pests*.—No susceptibility or resistance to diseases or pests has been observed.

*Root description*.—Fibrous, freely branched.

*Propagation*.—Grafting and chip budding.

*Root development*.—3 months for root initiation, 12 to 18 months from a plug to young plant.

*Growth rate*.—Vigorous.

Branch description:

*Branch shape*.—Round.

*Branch color*.—Young; 187A, older bark 198B, mature; striated with 166A and 164D, older bark 198B.

*Bark texture*.—Young stems; smooth with horizontal lenticels 187B in color, older bark; rugose.

*Branching*.—Main; 1, lateral; 6, weeping.

*Branch size*.—Main; 1.2 m in length, 3 cm in diameter, lateral; 50 cm in length, 3 mm in diameter.

Foliage description:

*Leaf shape*.—Elliptical.

*Leaf division*.—Simple.

*Leaf base*.—Generally rounded with some cordate and acute.

*Leaf apex*.—Acuminate at very tip.

*Leaf fragrance*.—None.

*Leaf burst*.—Early in the beginning of full flowering.

*Leaf venation*.—Pinnate, both surfaces 145C.

*Leaf margins*.—Biserrate.

*Leaf arrangement*.—Alternate, in clusters.

*Leaf aspect*.—Slightly concave and held horizontal to oblique downward in relation to shoot.

*Leaf attachment*.—Petiolate.

*Leaf surface*.—Both surfaces glossy, glabrous.

*Leaf size*.—Average of 13 cm in length and 8 cm in width.

*Leaf internodes*.—Average of 6 cm.

*Leaf color* (*both surfaces*).—After burst; 22A, young; 154A, lightly flushed with 153A, maturing; variegated, a blend of 136A, 143D, 145A, and 157C, fully mature; variegated with 136A and 157A, fall; variegated with 136A and 157A with margins suffused with 185C.

*Petioles*.—Up to 6 cm in length, 3 mm in diameter, glossy surfaces that are moderately pubescent, color; young N144A, mature 185A, aging to 187A.

Inflorescence description:

*Inflorescence type*.—Clusters of single flowers.

*Lastingness of inflorescence*.—An average of 5 days.

*Inflorescence size*.—Cluster of 3; 3 cm in depth, 5 cm in width.

*Flower fragrance*.—Faint.

*Flower quantity*.—Average of 3 per inflorescence.

*Flower type*.—Rotate corolla above an elongated calyx with stamens and pistil extended.

*Flower size*.—Average of 3 cm in diameter 2.5 cm in depth.

*Flower buds*.—2.1 cm in diameter, 1.3 cm in depth, color; oval in shape, glabrous surface, 68A and N144A in color.

*Calyx*.—Comprised of sepals fused into an ovoid base with un-fused portions spreading at apex.

*Sepals*.—5, glabrous surface, 5 mm in length with un-fused portions about 4 mm in width, lacerate margins, attenuate apex, fused base, color; young upper and lower surface N79B, 68A and 76D, mature upper and lower surface 65B and 76D.

*Petals*.—5, broadly elliptic in shape, un-fused, thin and papery substance, smooth margin, rounded base, emarginate apex, about 3 cm in length and 1.5 cm in width, color; opening and fully open upper surface NN155D, base flushed with 67B, opening and fully open lower surface NN155D.

*Pedicels*.—Average of 3 cm in length, 1 mm in diameter, 146D in color, glabrous surface, whorled arrangement from the stem.

Reproductive organs:

*Gynoecium*.—Pistil; 1, about 2 cm in length and extending beyond perianth, style; 150C in color, style and stigma together; 1 cm in length, stigma; <1 mm in diameter, 185A in color, ovary is superior, glabrous, 144B in color, nectarines; 2, kidney shaped, 46B in color.

*Androecium*.—Stamens; 20, base adnate to calyx, filaments; 56A in color, 2 cm in length and 1 mm in diameter, anthers; 163A in color, dorsifixed, 1 mm in length and <1 mm in width, pollen; abundant in quantity, 11B in color.

*Fertility*.—Self-fertile.

Fruit description: No fruit or seed has been produced to date.

It is claimed:

1. A new and distinct cultivar of *Prunus* tree named 'GEE001' as herein illustrated and described.

* * * * *